Figure 1:
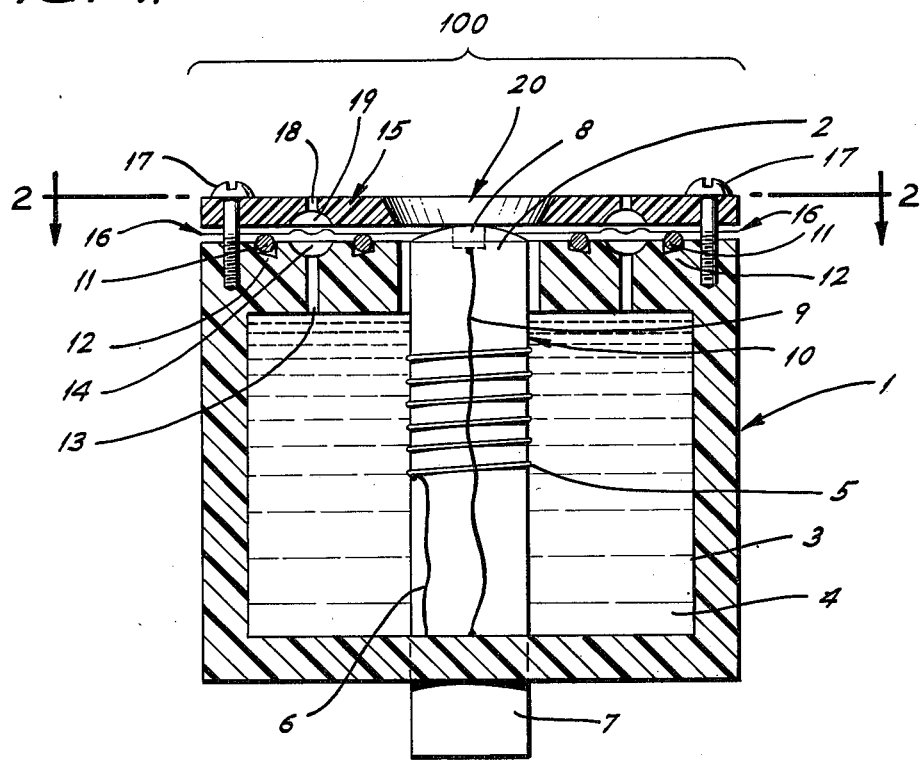

United States Patent [19]
Porter et al.

[11] 4,126,531
[45] Nov. 21, 1978

[54] SENSOR WITH ANNULAR PRESSURE COMPENSATING MEANS

[75] Inventors: Joe A. Porter, Whittier; Allen F. Dageforde, Orange, both of Calif.

[73] Assignee: Uniloc, Inc., Irvine, Calif.

[21] Appl. No.: 888,115

[22] Filed: Mar. 20, 1978

[51] Int. Cl.$^2$ .................. G01N 27/30; G01N 27/46
[52] U.S. Cl. .................................................. 204/195 P
[58] Field of Search ............... 204/195 P, 1 P; 324/29

[56] References Cited

U.S. PATENT DOCUMENTS

| | | | |
|---|---|---|---|
| 2,709,920 | 6/1955 | Moore | 73/432 HA |
| 3,510,421 | 5/1970 | Gealt | 204/195 P |
| 3,577,332 | 5/1971 | Porter et al. | 204/195 P |
| 3,929,603 | 12/1975 | Porter | 204/195 P |
| 3,997,419 | 12/1976 | Scott et al. | 204/195 P |
| 4,017,374 | 4/1977 | Aas et al. | 204/195 P |

*Primary Examiner*—G. L. Kaplan
*Attorney, Agent, or Firm*—Alexander D. Ricci; Steven H. Markowitz

[57] ABSTRACT

The present invention is directed to a means for compensating for pressure changes in sensing devices. To assure accurate measurements with sensing devices immersed in a medium, it is necessary to have external and internal pressures preferably the same or very close. This invention provides pressure compensation through the use of at least one but preferably a plurality of passages communicating the exterior to the interior of the cell. The passage preferably but not necessarily is so designed as to provide an inner portion of the passage with a greater dimension than the remainder. In the greater dimensioned portion of the passage is positioned a substantially non-tensioned membrane so as to provide a separation or barrier between the interior and exterior of the cell.

21 Claims, 2 Drawing Figures

SENSOR WITH ANNULAR PRESSURE COMPENSATING MEANS

BACKGROUND OF THE INVENTION

The present invention is directed to sensoring apparatus which find utility in measuring various aspects of liquid or gaseous mediums. More specifically, the invention provides a means for pressure compensating an amperometric sensor which utilizes a semi-permeable membrane to separate the internal elements and the electrolyte contained therein (and enveloping the elements) from the media being sampled, monitored or analyzed. In this regard reference is hereby made to U.S. Pat. Nos. 3,510,421; 3,577,332; and 3,929,603 which are hereby incorporated by reference and which comprehensively describe the type of measurements or analyses which are commonly made utilizing these means. In addition, these patents also disclose the type membranes and barriers commonly used in the sensors. In addition, U.S. Pat. No. 3,577,332 to Porter et al points out the need for pressure compensating means and procedures and the problems incurred where this is not adequately provided for.

Sensors of the type described and to which the present invention is directed require that the membrane be maintained in a very stable relationship with respect to the surface of the cathode element.

Since the membranes used generally range from less than one to five thousandths inch in thickness, they are obviously quite fragile. Subjecting such a sensor to a pressure differential between the inside and outside will therefore cause movement of the membrane and a resultant change in sensor output.

In order to avoid the above problem and maintain sensor stability, it is necessary to provide a pressure communications path between the electrolyte and the external environment. Such a path may be as simple as a poorly sealed membrane, a drilled passage through the body, or a somewhat more elaborate opening sealed with a flexible diaphraghm. While all of these schemes will provide pressure compensation, they suffer such problems as electrolyte leakage, non-electrical isolation when used in liquid systems, and, in the case of the diaphragm seal, a limited range of pressure compensation.

GENERAL DESCRIPTION OF THE INVENTION

As earlier described, various means have been utilized for pressure compensation purposes in sensing devices. However, each of the systems has apparent disadvantages in that they are very specifically designed, require specifically tooled pieces, are costly, and/or require a fair amount of time to assemble. This is true whether the means is a diaphragm seal or an elongated eliptical tube, as disclosed in U.S. Pat. Nos. 3,577,332 and 3,929,603 respectively. In addition, the diaphragm method provides a limited pressure compensation while the tubular methods, although sufficiently sensitive, require expensive tooling for their parts. The present inventors' goal was to provide a sensor which possessed adequate and sensitive response to pressure changes and which was of relatively simple design to assure ease of assembly without the need for parts requiring sophisticated tooling.

Applicants discovered that if the cell was designed so as to have at least one but preferably a plurality of passages from its exterior to its interior communicating with the reservoir (containing the electrolyte) and the passage was so designed to permit the positioning of a substantially non-tensioned membrane, even acute pressure compensation could be achieved because of the direct effect on a significant portion of the electrolyte solution. The design not only provided the obtention and maintenance of zero pressure differential across the membranes but permitted these results to be achieved with a system of relatively simple design.

The invention can be highlighted by describing such in a typical arrangement. The cell comprises
  (i) an electrically non-conductive body having an electrolyte reservoir therein,
  (ii) a pair of spaced electrodes positioned in said reservoir and adapted to be joined by an electrolyte in said reservoir,
  (iii) an opening communicating between said reservoir and the exterior of said body,
  (iv) a thin flexible polymeric membrane permeable to said constituent and impermeable to the electrolyte,
  (v) mounting means maintaining said membrane under tension over one electrode which is disposed in said opening and in a position to close said opening, the improvement comprising a passage or passages disposed in said body preferably around said electrode in said opening and communicating between said reservoir and the exterior of said body, the mounting means having an opening corresponding to the opening in said body and also having a passage or passages which extend from its exterior to its interior, which passage(s) communicates with and corresponds in configuration and circumferential dimension with the passage in the body, and said membrane being held by said mounting means between the exterior of said body and the interior of said mounting means.

As apparent from the above description, the membranes positioned over the opening and in the passage are one and the same and preferably one piece cut to match the shape and size of the body and mounting means. For ease of assembly it is desirable to have one piece of membrane which is thus easily tensioned by the mounting means not only over the electrode but in a slackened position to act as the pressure compensation means. Utilizing the same membrane moreover insures that the pressure changes will be consistently reflected on both the tensioned and the untensioned portions since both of course are made of the same material.

In a preferred embodiment, the passage or passages in both the body and the mounting means are designed so as to provide the passage(s) with a differential in size. More specifically, the passage in the exterior of the body is somewhat larger in dimension than the remaining of the passage communicating with the reservoir. Likewise, the passage(s) on the interior of the mounting means is larger in dimension than the passage on its exterior. The passages, for uniformity, in the body and the mounting means should correspond in configuration and dimension. The membrane for pressure compensation is held in the larger dimensioned area also in a non-tensioned manner. This design is preferred for production and assembly purposes and accordingly is the embodiment featured in the drawings.

In order to provide the membrane over the opening with the proper tension, the technique patented in U.S. Pat. No. 3,887,194, which is hereby incorporated by reference, is employed. It should also be noted that modification of the technique of the patent also permits the attainment of the loose, non-tensioned membrane in the pressure compensating passages. More specifically, the O-ring which provides tensioning of the membrane over the electrode is placed in an annular groove having a floor angled (from small depth to greater depth) away from the electrode. The annular groove (outside of the pressure compensating passages) bearing the O-ring which holds the membrane for the pressure compensating passage is angled toward the electrode opening, i.e., small depth on outside with greater depth of groove towards the interior of the cell. Operationally what happens upon tightening of the mounting means over the O-rings in the groove is that the O-rings in the groove holding the membrane are compressed and flow away from the electrode, thus tensioning such over the electrode. In contrast, the O-rings in the groove holding the membrane in the passages, when compressed, flow toward the center of the cell, thereby pushing the membrane to the center of the passage. Accordingly, the non-tensioned feature is attained.

To fully realize the advantages of the present invention there are three membrane areas to be considered: the first membrane area (hereafter referred to as the "passage area") is that which is contained between the passages; the second area (referred to as the "total opening area") is that area of the membrane which seals the body opening; and the third area (referred to as the "unsupported opening area") is that membrane area which seals the body opening but which is not in contact with the supporting element or electrode. It is desirable that the passage area be larger within reason than the unsupported opening area. This assures a greater area of response to pressure changes and movement of the membrane within the passages is preferential to that over the cathode. It is this feature which of course determines the number, size and depth of the respective passages. If the passages differ in size as depicted in FIG. 1, the only critical parameter that must be observed is to assure that smaller passages are large enough to provide no restriction to fluid flow and thus assure rapid response of the membrane to changes in pressure.

SPECIFIC EMBODIMENTS

FIG. 1 is an enlarged vertical cross-sectional view of the electrochemical cell depicting passages with different circumferential dimensions. More specifically, Cell 100 is composed of cylindrical, electrically non-conductive body 1 and mounting means or cap 15. Body 1 has opening 2 and reservoir 3 which contains electrolyte 4. Electrode 5 (normally the anode) is depicted in the form of a helical wire but may be an embedded electrode and is wrapped around central electrically non-conductive element 10 which leads to terminal 7. Electrode 8 (normally the cathode) is embedded in and flush with the end of element 10. Electrodes 5 and 8 are connected to terminal 7 by means of conductors 6 and 9 respectively. Terminal 7 includes well-known appropriate electrical connections, not shown, for connecting the cell to an external circuit. Body 1 contains grooves 12 fitted with O-rings 11 which obviously allows cap or mounting means 15 to securely fasten and tension membrane 16 against electrode 8 and body 1. The grooves 12 are depicted as having a floor angled approximately 10° in accordance with the invention of U.S. Pat. No. 3,887,194. The smaller depth of the groove is inward toward the opening which permits the O-ring to roll outward and thus provide the appropriate tension. It will be noted that the outside grooves are angled opposite (smallest depth farthest away from the opening) to permit the obtention of the loose or non-tensioned membrane in the dimensional space in the combined passages.

In accordance with the invention, cap 15, which has an opening 20 concentric with electrode 8 as viewed from the cap side of the cell (FIG. 2) possesses passages as part of the pressure compensation design. Passage 13 through body 1 terminates at the exterior of the body with larger dimensional portion of passage 14. Likewise, cap 15 has passage 18 from its exterior to its interior where it terminates as larger dimensional portion of passage 19. Although the Figure illustrates two such passages, it is obvious that one but preferably a plurality of individual passages as described may be utilized. It is apparent that as the number of passages or areas thereof increases, the sensitivity to pressure change is enhanced.

Figure 2:
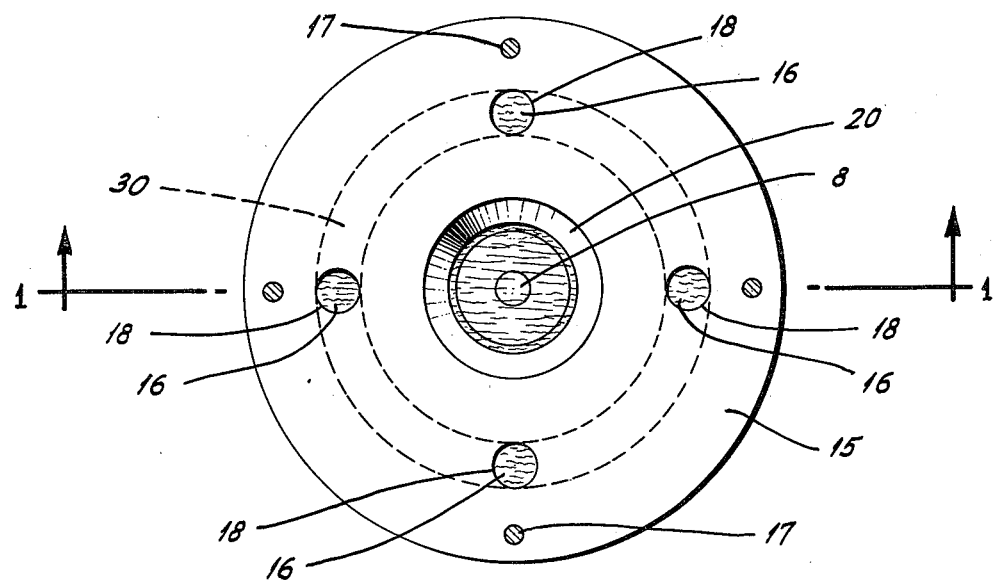

FIG. 2 is a view of the electrode cap side of the cell. Cap 15 is bolted to body 1 (not shown) by bolts 17. Opening 20 of cap surrounds concentrically supporting central element 10 bearing electrode 8, both of which are covered by membrane 16. Disposed around opening 20 and electrode 8 are passages 18 in cap 15, exposing membrane 16 which is positioned beneath cap 15. Also depicted by way of broken lines 30 is a preferred method of producing the larger dimensional cavities or passages earlier described. Since the objective of the invention is to provide a pressure compensation system which is easily assembled, it is desirable in machining the body 1 and cap 15 is also machine a channel of semi-circular cross-sectional shape and of particular and corresponding dimensions in each annular to the respective openings of the cap and body. This channel is depicted as 30 in FIG. 2 and if the larger dimensional cavity is considered annular in FIG. 1 it would be respectively 14 and 19. It is apparent that if this preferred method is utilized, then all that is required to produce the pressure compensating passages is merely the drilling of passages 18 and 13 through cap 15 and body 1. When a one-piece membrane is utilized for both sensing and pressure compensation, it is apparent that the assembly is quite simple and completed rather quickly.

| Typical Dimensions of Standard Oxygen Cell | |
|---|---|
| Length of Cell with cap (100) | 3 inches |
| Diameter of Cell 100 | 1 1/2 inches |
| Diameter of opening 20 | 3/8 inch |
| Diameter of passages 14 and 19 (or width of groove 30) | 1/8 inch |
| Length of passage 18 | 1/16 inch |
| Depth and width of channel 30 (or passages 14 and 19) | 1/16 inch |
| Diameter of non-conductive element 10 | slightly less than 3/8 inch |
| Diameter of electrode 8 | 5/16 inch |
| Length of passage 13 | 3/8 inch |
| Depth and width of channels | 1/16 inch |

While we have shown and described several embodiments in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

What is claimed is:

1. A cell for electrochemical analysis of a constituent in a sample comprising
   (i) an electrically non-conductive body having an electrolytic reservoir therein,
   (ii) a pair of spaced electrodes positioned in said reservoir and adapted to be joined by an electrolyte in said reservoir,
   (iii) an opening communicating between said reservoir and the exterior of said body,
   (iv) a thin flexible polymeric membrane permeable to said constituent and impermeable to the electrolyte, and
   (v) mounting means maintaining said membrane under tension over one electrode which is disposed in said opening and in a position to close said opening, the improvement comprising at least one body passage disposed in said body and communicating between said reservoir and the exterior of said body, the mounting means having an opening corresponding to the opening in said body and at least one passage corresponding in configuration and dimension with said body passage and communicating with said body passage, and a membrane being compressed by said mounting means between the exterior of said body and the interior side of said mounting means so as to provide a flexible, substantially non-tensioned separation between the exterior of said mounting means and said reservoir.

2. A cell according to claim 1, wherein the electrodes are supported on an electrically non-conducting centrally located element positioned so that one end is in said opening.

3. A cell according to claim 2, wherein one electrode is embedded in said element at the end positioned in said opening and said membrane closing said openings is in contact and is supported by said electrode and said element.

4. A cell according to claim 1, wherein the total area of the passage membrane is the same or greater than the total opening area thereof.

5. A cell according to claim 1, wherein the mounting means and the body are each provided with a channel, semi-circular in shape, which is annular to the respective openings, which channel serves as the area of the passage of the mounting means and of the body, where the membrane of the passage is positioned.

6. A cell according to claim 5, wherein the total area of the passage membrane is the same as or greater than the total opening area thereof.

7. A cell according to claim 6, wherein the electrodes are supported on an electrically non-conducting, centrally located element positioned so that one end is in said opening.

8. A cell according to claim 7, wherein one electrode is embedded in said element at the end positioned in said opening and said membrane closing said opening is in contact and substantially supported by said electrode and said element.

9. A cell according to claim 1, wherein the area of said membrane in said passage is equal to or greater than the area of the membrane in said opening which is not supported by said electrode.

10. A cell according to claim 9, wherein the electrodes are supported on an electrically non-conducting, centrally located element positioned so that one end is in said opening.

11. A cell according to claim 10, wherein one electrode is embedded in said element at the end positioned in said opening and said membrane closing said opening is in contact and being substantially supported by said electrode and said element.

12. A cell according to claim 11, wherein the mounting means and the body are provided with a channel, semi-circular in shape, which is annular to the respective openings, which channel serves as the area of the passage of the mounting means and the body where the membrane of the passage is positioned.

13. A cell according to claim 1, wherein the body of the cell is provided with (i) a groove annular to the opening which is fitted with an O-ring, said groove having a floor angled so as to have a greater depth away from said opening, and (ii) a second groove fitted with an O-ring annular to said passage, said groove having a floor angled so as to provide the greater depth toward said opening, to assure when said O-rings are compressed by said mounting means that the membrane is tensioned in said opening but substantially non-tensioned and slack in said passage.

14. A cell according to claim 13, wherein the floors of the grooves are angled to about 10°.

15. A cell for electrochemical analysis of a constituent in a sample comprising
   (i) an electrically non-conductive body having an electrolytic reservoir therein,
   (ii) a pair of spaced electrodes positioned in said reservoir and adapted to be joined by an electrolyte in said reservoir,
   (iii) an opening communicating between said reservoir and the exterior of said body,
   (iv) a thin flexible polymeric membrane permeable to said constituent and impermeable to the electrolyte, and
   (v) mounting means maintaining said membrane under tension over one electrode which is disposed in said opening and in a position to close said opening, the improvement comprising at least one body passage disposed in said body and communicating between said reservoir and the exterior of said body with a portion of the passage on the exterior of said body being of a larger dimension than the remaining portion of said passage communicating with the reservoir, the mounting means having an opening corresponding to the opening in said body and having at least one mounting means passage which extends from an exterior side thereof to an interior side thereof, said passage corresponding in configuration and dimension with said body passage and communicating with said body passage, and a membrane being compressed by said mounting means between the exterior of said body and the interior side of said mounting means and in said larger dimensional portions of both passages so as to provide a flexible, substantially non-tensioned separation between the exterior of said mounting means and said reservoir.

16. A cell according to claim 15, wherein the electrodes are supported on an electrically non-conducting, centrally located element positioned so that one end is in said opening, and wherein one electrode is embedded in said element at the end positioned in said opening and said membrane closing said openings is in contact and is supported by said electrode and said element.

17. A cell according to claim 15, wherein the total area of the passage membrane is the same or greater than the total opening area thereof.

18. A cell according to claim 15, wherein the mounting means and the body are each provided with a channel, semi-circular in shape, which is annular to the respective openings, which channel serves as the larger dimensional area portions of the passage of the mounting means and of the body, and which channels are connected to the interior and exterior of the cell by the small dimensional passages.

19. A cell according to claim 18, wherein the total area of the passage membrane is the same as or greater than the total opening area thereof.

20. A cell according to claim 15, wherein the body of the cell is provided with a groove annular to the opening which is filled with an O-ring, said groove having a floor angled so as to have a greater depth away from said opening, and a second groove filled with an O-ring annular to said passages, said groove having a floor angled so as to provide the greater depth toward said opening, to assure when said O-rings are compressed by said mounting means that the membrane is tensioned in said opening but substantially non-tensioned and slack in said passage.

21. A cell according to claim 20, wherein the floors of the grooves are angled to about 10°.

* * * * *